(12) United States Patent
Zenke et al.

(10) Patent No.: US 9,475,744 B2
(45) Date of Patent: Oct. 25, 2016

(54) METHOD FOR RECOVERING FLUORINE-CONTAINING ETHER

(71) Applicant: DAIKIN INDUSTRIES, LTD., Osaka-shi, Osaka (JP)

(72) Inventors: Yumi Zenke, Settsu (JP); Tadaharu Isaka, Settsu (JP); Ryouichi Fukagawa, Settsu (JP); Takeshi Shimono, Settsu (JP)

(73) Assignee: DAIKAN INDUSTRIES, LTD., Osaka (JP)

( * ) Notice: Subject to any disclaimer, the term of this patent is extended or adjusted under 35 U.S.C. 154(b) by 0 days.

(21) Appl. No.: 14/654,238

(22) PCT Filed: Jan. 20, 2014

(86) PCT No.: PCT/JP2014/050946
§ 371 (c)(1),
(2) Date: Jun. 19, 2015

(87) PCT Pub. No.: WO2014/115679
PCT Pub. Date: Jul. 31, 2014

(65) Prior Publication Data
US 2015/0376100 A1      Dec. 31, 2015

(30) Foreign Application Priority Data

Jan. 23, 2013   (JP) ................................. 2013-010557

(51) Int. Cl.
| | | |
|---|---|---|
| *C07C 41/40* | (2006.01) | |
| *C08F 14/20* | (2006.01) | |
| *C08F 14/22* | (2006.01) | |
| *C08F 14/18* | (2006.01) | |
| *C08F 14/26* | (2006.01) | |
| *C08F 14/28* | (2006.01) | |
| *C07C 41/34* | (2006.01) | |
| *C08F 6/00* | (2006.01) | |
| *C08F 6/16* | (2006.01) | |
| *C08F 6/24* | (2006.01) | |
| *C08F 6/28* | (2006.01) | |
| *C08F 214/26* | (2006.01) | |
| *C08F 214/28* | (2006.01) | |

(52) U.S. Cl.
CPC .............. *C07C 41/40* (2013.01); *C07C 41/34* (2013.01); *C08F 6/008* (2013.01); *C08F 6/16* (2013.01); *C08F 6/24* (2013.01); *C08F 6/28* (2013.01); *C08F 14/18* (2013.01); *C08F 14/185* (2013.01); *C08F 14/20* (2013.01); *C08F 14/22* (2013.01); *C08F 14/26* (2013.01); *C08F 14/28* (2013.01); *C08F 214/262* (2013.01); *C08F 214/282* (2013.01)

(58) Field of Classification Search
None
See application file for complete search history.

(56) References Cited

U.S. PATENT DOCUMENTS

| | | |
|---|---|---|
| 6,258,907 B1 | 7/2001 | Funaki et al. |
| 2014/0100344 A1 | 4/2014 | Aida et al. |

FOREIGN PATENT DOCUMENTS

| | | | |
|---|---|---|---|
| CN | 102015779 A | 4/2011 | |
| JP | 07-504224 A | 5/1995 | |
| JP | 11-92507 A | 4/1999 | |
| JP | 11-235720 A | 8/1999 | |
| JP | 2001-261714 A | 9/2001 | |
| JP | 2005-29704 A | 2/2005 | |
| JP | 2010-501673 * | 1/2010 | ............... C08F 2/04 |
| JP | 2010-501673 A | 1/2010 | |
| WO | 93/17053 A1 | 9/1993 | |
| WO | 2008/024602 A1 | 2/2008 | |
| WO | 2009/137734 A1 | 11/2009 | |
| WO | 2012/173153 A1 | 12/2012 | |

OTHER PUBLICATIONS

The Free Dictionary (definition for Granulation obtained Mar. 3, 2016 from http://encyclopedia1.thefreedictionary.com/Granulation, pp. 1-3, 2003).*
International Preliminary Report on Patentability dated Aug. 6, 2015 issued by the International Bureau of WIPO in counterpart International Application No. PCT/JP2014/050946.
Mark W. Grenfell, "Hydrofluoroethers as Fluoromonomer Reaction Media", Research Disclosure, Jan. 1998, pp. 80-83, XP-000772402.
International Search Report for PCT/JP2014/050946 dated Mar. 11, 2014.
Communication dated Jul. 14, 2016 from the European Patent Office issued in corresponding Application No. 14743976.4.

* cited by examiner

*Primary Examiner* — Rosalynd Keys
(74) *Attorney, Agent, or Firm* — Sughrue Mion, PLLC (57) ABSTRACT

An object of the present invention is to provide a method for recovering a fluorine-containing ether capable of recovering a fluorine-containing ether used for producing a fluoropolymer, in higher recovery yield and in a shorter time. The present invention relates to a method for recovering a fluorine-containing ether, including the steps of: producing a wet fluoropolymer by suspension polymerization, solution polymerization, or bulk polymerization in the presence of at least a specific fluorine-containing ether; vaporizing and discharging vaporizable substances including the fluorine-containing ether by heating the wet fluoropolymer in a container; and transferring the vaporizable substances in the vaporized state to a cooling means to cool the vaporizable substances.

7 Claims, 1 Drawing Sheet

METHOD FOR RECOVERING FLUORINE-CONTAINING ETHER

CROSS REFERENCE TO RELATED APPLICATIONS

This application is a National Stage of International Application No. PCT/JP2014/050946 filed Jan. 20, 2014, claiming priority based on Japanese Patent Application No. 2013-010557 filed Jan. 23, 2013, the contents of all of which are incorporated herein by reference in their entirety.

TECHNICAL FIELD

The present invention relates to a method for recovering a fluorine-containing ether. More specifically, the present invention relates to a method for recovering a fluorine-containing ether used for producing fluoropolymers.

BACKGROUND ART

Emulsion polymerization and suspension polymerization are known as production methods of fluoropolymers. In these polymerization methods, perfluorocarbon (PFC) or chlorofluorocarbon (CFC) has been used as a polymerization medium. PFC and CFC however have a high global warming potential (GWP), and CFC also has a high ozone depletion potential. Therefore, it is preferred to reduce the amounts of these to be used. Further, since PFC and CFC are likely to adsorb on fluoropolymers, they are released and vaporized from fluoropolymers to form bubbles in the fluoropolymers when the fluoropolymers are extruded. As a result, PFC and CFC causes molding failures. Therefore, solvents alternative to PFC and CFC have been suggested.

Patent Literature 1 suggests a polymerization method that includes bringing a fluoromonomer into contact with a solvent that contains carbon; fluorine; at least one hydrogen atom; at least as many fluorine atoms as hydrogen atoms; no more than two adjacent —$CH_2$— groups; no hydrogen atoms on any primary carbon; and no methyl (—$CH_3$) groups, except as the grouping —$CF_2OCH_3$.

Patent Literature 2 suggests, in order to produce a fluoropolymer by polymerization in a polymerization medium, a production method of a fluoropolymer, in which (perfluoroalkyl)alkyl ether such as $F(CF_2)_4OCH_3$, $F(CF_2)_4OC_2H_5$, $(CF_3)_2CFOCH_3$, and $F(CF_2)_3OCH_3$, is used as a polymerization medium.

Further, in the above described production methods of fluoropolymers using polymerization mediums, it is preferred that the polymerization medium is separated, recovered, and recycled after a polymerization reaction in view of economic and environmental benefits. Thus, a polymerization medium recovery method is known.

Patent Literature 3 discloses a production method of a fluorocopolymer including copolymerizing tetrafluoroethylene with a specific fluorine-containing vinyl ether using perfluoroheptane as a reaction solvent in the presence of a chain transfer agent in an amount of 0.5 to 4 mol % based on the total amount of the fed monomers, and discloses recovery of the reaction solvent after the polymerization reaction in the method.

Patent Literature 4 discloses a method for producing fluoropolymers, comprising polymerizing at least one fluorinated monomer to yield a fluoropolymer in a polymerization medium including water and a specified low-telogenic hydrofluoroether (HFE), and the method further comprises separating the fluoropolymer and water from the HFE solvent by distillation of the HFE solvent while the fluoropolymer is agglomerated, and reusing the HFE solvent for another polymerization method.

CITATION LIST

Patent Literature

Patent Literature 1: JP H7-504224 T
Patent Literature 2: JP H11-92507 A
Patent Literature 3: JP 2001-261714 A
Patent Literature 4: JP 2010-501673 T

SUMMARY OF INVENTION

Technical Problem

As described above, recovery of solvents used for producing fluoropolymers is known. However, in the case of using perhalogenated carbons such as perfluoroheptane as a solvent as described in Patent Literature 3, they are difficult and take a long time to recover, and are recovered with low recovery efficiency because perhalogenated carbons are difficult to separate from fluoropolymers to be likely to remain in the fluoropolymers even if vaporized by heating. Further, perhalogenated carbons, which have a low latent heat of vaporization and are likely to volatilize, are poorly recovered through condensation by cooling. On the other hand, fluorine-containing ethers, which have a latent heat of vaporization higher than perhalogenated carbons, can be recovered in higher recovery efficiency through condensation by cooling as compared to perhalogenated carbons. However, the method in Patent Literature 4 needs to be further improved in order to reduce the recovery time and sufficiently raise the recovery efficiency.

The present invention has been made in view of the current state of the art described above, and an object of the present invention is to provide a method for recovering a fluorine-containing ether capable of recovering a fluorine-containing ether used for producing a fluoropolymer, in higher recovery yield and in a shorter time.

Solution to Problem

The present inventors have performed various examinations on the process capable of recovering a fluorine-containing ether used for producing fluoropolymers, in higher recovery yield and a shorter time. As a result of the examinations, they have found that a fluorine-containing ether is easily separated from a fluoropolymer in such a way that a specific fluorine-containing ether is used as a fluorine-containing ether, a wet fluoropolymer produced is heated in a container to vaporize and discharge vaporizable substances including the fluorine-containing ether, and the vaporizable substances in the vaporized state are transferred to a cooling means to be cooled. Thus, the fluorine-containing ether can be recovered without waste. In this way, the fluorine-containing ether can be recovered in higher recovery yield and in a shorter time as a result of producing a wet fluoropolymer by suspension polymerization, solution polymerization, or bulk polymerization in the presence of a specific fluorine-containing ether; vaporizing and discharging vaporizable substances including the fluorine-containing ether by heating the wet fluoropolymer in a container; and transferring the vaporizable substances in the vaporized state to a cooling means to cool the vaporizable substances. Thus, the present inventors admirably solved the above problems, and the present invention has been completed.

That is, the present invention relates to a method for recovering a fluorine-containing ether, including the steps of: producing a wet fluoropolymer by suspension polymerization, solution polymerization, or bulk polymerization in the presence of at least a fluorine-containing ether represented by the formula (1):

$$Rf-O-R \quad (1)$$

wherein Rf represents a C2-C6 fluoroalkyl group or a C2-C6 alkyl group, and R represents a C1-C4 fluoroalkyl group or a C1-C4 alkyl group, provided that the total number of carbon atoms in Rf and R is at most 8; vaporizing and discharging vaporizable substances including the fluorine-containing ether by heating the wet fluoropolymer in a container; and transferring the vaporizable substances in the vaporized state to a cooling means to cool the vaporizable substances.

The fluoropolymer preferably has a polymerization unit derived from at least one fluoromonomer selected from the group consisting of tetrafluoroethylene, hexafluoropropylene, vinylidene fluoride, chlorotrifluoroethylene, (perfluoromethyl)vinyl ether, (perfluoroethyl)vinyl ether, (perfluoropropyl)vinyl ether, trifluoroethylene, vinyl fluoride, perfluoro(alkyl vinyl ethers) represented by the formula (2-1):

$$CF_2=CFO(CF_2CF(Y)O)_m(CF_2)_nF \quad (2-1)$$

wherein Y represents a fluorine atom or a trifluoromethyl group, m is an integer of 0 to 2, and n is an integer of 1 to 4, monomers represented by the formula (2-2):

$$CH_2=CF(CF_2)_nZ \quad (2-2)$$

wherein Z represents a fluorine atom or a hydrogen atom, and n is an integer of 1 to 8, and monomers represented by the formula (2-3):

$$CH_2=CH(CF_2)_nZ \quad (2-3)$$

wherein Z represents a fluorine atom or a hydrogen atom, and n is an integer of 1 to 8.

The method for recovering preferably further includes, but is not particularly limited to, transferring the vaporizable substances liquefied by cooling in the cooling step to a distillation means to distill the vaporizable substances.

A value of x/V is preferably at most 0.140, wherein V represents the inner volume (L) of the container, and x represents the discharge rate (kg/hour) of the vaporizable substances from the container.

A fluorine-containing compound having a boiling point lower than the boiling point of the fluorine-containing ether is preferably added to the wet fluoropolymer.

The method for recovering preferably further includes, but is not particularly limited to, transferring the vaporizable substances vaporized in the vaporizing step to a compression means to compress the vaporizable substances.

The compression means is preferably, but is not particularly limited to, a compressor.

The cooling means is preferably, but is not particularly limited to, a condenser.

Advantageous Effects of Invention

The method for recovering of the present invention has the above configuration. Therefore, a fluorine-containing ether used for producing a fluoropolymer can be recovered in higher recovery yield and in a shorter time.

DESCRIPTION OF EMBODIMENTS

The method for recovering of the present invention includes producing a wet fluoropolymer by suspension polymerization, solution polymerization, or bulk polymerization in the presence of at least a specific fluorine-containing ether.

The fluorine-containing ether is represented by the formula (1):

$$Rf-O-R \quad (1)$$

wherein Rf represents a C2-C6 fluoroalkyl group or a C2-C6 alkyl group, and R represents a C1-C4 fluoroalkyl group or a C1-C4 alkyl group, provided that the total number of carbon atoms in Rf and R is at most 8.

Rf in the formula (1) is preferably a C2-C5 fluoroalkyl group or a C2-C5 alkyl group, more preferably a C3-C4 fluoroalkyl group, and still more preferably a C4 fluoroalkyl group.

R in the formula (1) is preferably a C1-C3 fluoroalkyl group or a C1-C3 alkyl group, more preferably a C1-C2 alkyl group, and still more preferably a C1 alkyl group.

The total number of carbon atoms in Rf and R in the formula (1) is preferably 3 to 7, more preferably 4 to 6, and still more preferably 5.

In the fluorine-containing ether, the number of fluorine atoms is preferably 50% or more, more preferably 60% or more, and still more preferably 70% or more of the total number of hydrogen atoms and fluorine atoms.

The fluorine-containing ether has a low global warming potential, no ozone depletion potential, and low chain transfer activity. Use of the fluorine-containing ether allows efficient production of a fluoropolymer having a high molecular weight, and excellent solvent resistance and chemical resistance.

The fluorine-containing ether is preferably at least one selected from the group consisting of fluorine-containing ethers represented by the formula (1-1):

$$F(CF_2)_pO(CH_2)_qH \quad (1-1)$$

wherein p is an integer of 2 to 6, and q is an integer of 1 to 4, fluorine-containing ethers represented by the formula (1-2):

$$H(CF_2)_pO(CF_2)_qF \quad (1-2)$$

wherein p is an integer of 2 to 6, and q is an integer of 1 to 4, fluorine-containing ethers represented by the formula (1-3):

$$H(CF_2)_pO(CH_2)_qH \quad (1-3)$$

wherein p is an integer of 2 to 6, and q is an integer of 1 to 4, fluorine-containing ethers represented by the formula (1-4):

$$X(CF_2)_pCH_2O(CF_2)_qH \quad (1-4)$$

wherein X represents a fluorine atom or a hydrogen atom, p is an integer of 1 to 5, and q is an integer of 1 to 4, $(CF_3)_2CHOCH_3$, $(CF_3)_2CFOCH_3$, $CHF_2CF_2CH_2OCF_2CHF_2$, $CF_3CHFCF_2OCH_3$, and $CF_3CHFCF_2OCF_3$.

More preferred are $C_4F_9OCH_3$, $C_4F_9OC_2H_5$, $C_3F_7OCH_3$, and $(CF_3)_2CFOCH_3$, and still more preferred is $C_4F_9OCH_3$.

The fluorine-containing ether has a boiling point of preferably −20° C. to 85° C., more preferably 0° C. to 85° C., and still more preferably 4° C. to 85° C. A fluorine-containing ether having a boiling point in the above ranges is easily separated from a solvent such as water when vaporizable substances are recovered through the vaporization after polymerization.

The fluorine-containing ether can be used as a polymerization solvent. The amount of the fluorine-containing ether is appropriately selected depending on the type and characteristics of a target polymer. The fluorine-containing ether may be mixed with other polymerization solvents. Further, the fluorine-containing ether in which a polymerization initiator is preliminary dissolved may be fed to a reaction vessel. That is, the fluorine-containing ether can be used as a solvent for an initiator.

The wet fluoropolymer is produced by suspension polymerization, solution polymerization, or bulk polymerization of a fluoromonomer. Among these polymerization methods, suspension polymerization is preferred.

The fluoromonomer is preferably at least one fluoromonomer selected from the group consisting of tetrafluoroethylene (TFE), hexafluoropropylene (HFP), vinylidene fluoride (VdF), chlorotrifluoroethylene (CTFE), (perfluoromethyl)vinyl ether, (perfluoroethyl)vinyl ether, (perfluoropropyl)vinyl ether, trifluoroethylene, vinyl fluoride, perfluoro(alkyl vinyl ethers) represented by the formula (2-1):

$$CF_2=CFO(CF_2CF(Y)O)_m(CF_2)_nF \qquad (2\text{-}1)$$

wherein Y represents a fluorine atom or a trifluoromethyl group, m is an integer of 0 to 2, and n is an integer of 1 to 4, monomers represented by the formula (2-2):

$$CH_2=CF(CF_2)_nZ \qquad (2\text{-}2)$$

wherein Z represents a fluorine atom or a hydrogen atom, and n is an integer of 1 to 8, and monomers represented by the formula (2-3):

$$CH_2=CH(CF_2)_nZ \qquad (2\text{-}3)$$

wherein Z represents a fluorine atom or a hydrogen atom, and n is an integer of 1 to 8.

In the formula (2-1), m is preferably an integer of 0 or 1, and more preferably 0. Further, n is preferably an integer of 1 to 3.

In the formula (2-2), Z is preferably a hydrogen atom. Further, n is preferably an integer of 1 to 6, and more preferably an integer of 1 to 4.

In the formula (2-3), Z is preferably a fluorine atom. Further, n is an integer of 1 to 6, and more preferably an integer of 1 to 4.

The fluoropolymer is preferably a fluororesin. The fluororesin may be any resin having a clear melting point.

The fluoropolymer has a melting point of preferably 100° C. to 347° C., and more preferably 110° C. to 322° C.

The melting point can be determined as a temperature corresponding to the maximum value in the melting heat curve measured at a temperature rise of 10° C./min using a DSC device (produced by Seiko Instruments Inc.).

The fluoropolymer preferably has a melt flow rate (MFR) of 1 to 100 g/10 min.

The MFR can be measured under a load of 5.0 kg in accordance with ASTM D 3307. The temperature for measurement varies depending on the melting point of the fluoropolymer.

The fluoropolymer preferably has a polymerization unit derived from at least one fluoromonomer selected from the group consisting of tetrafluoroethylene [TFE], hexafluoropropylene [HFP], vinylidene fluoride [VdF], chlorotrifluoroethylene [CTFE], (perfluoromethyl)vinyl ether, (perfluoroethyl)vinyl ether, (perfluoropropyl)vinyl ether, trifluoroethylene, vinyl fluoride, perfluoro(alkyl vinyl ethers) represented by the formula (2-1):

$$CF_2=CFO(CF_2CF(Y)O)_m(CF_2)_nF \qquad (2\text{-}1)$$

wherein Y represents a fluorine atom or a trifluoromethyl group, m is an integer of 0 to 2, and n is an integer of 1 to 4, monomers represented by the formula (2-2):

$$CH_2=CF(CF_2)_nZ \qquad (2\text{-}2)$$

wherein Z represents a fluorine atom or a hydrogen atom, and n is an integer of 1 to 8, and monomers represented by the formula (2-3):

$$CH_2=CH(CF_2)_nZ \qquad (2\text{-}3)$$

wherein Z represents a fluorine atom or a hydrogen atom, and n is an integer of 1 to 8.

The polymerization unit derived from a monomer used herein represents a form in which a carbon-carbon unsaturated double bond in a monomer molecule is replaced by a single bond.

The fluoropolymer may have a polymerization unit derived from a non-fluorinated monomer. In view of keeping the heat resistance, the chemical resistance, and other properties, the fluoropolymer may include a polymerization unit derived from an ethylenic monomer having 5 or less carbon atoms. Such an embodiment is one preferred embodiment. The fluoropolymer preferably also has a polymerization unit derived from at least one non-fluorinated monomer selected from the group consisting of ethylene [Et], propylene, 1-butene, 2-butene, alkyl vinyl ether, vinyl chloride, vinylidene chloride, and unsaturated carboxylic acids.

The fluoropolymer is preferably at least one selected from the group consisting of TFE/HFP copolymers [FEP], TFE/perfluoro(alkyl vinyl ether) copolymers [PFA], Et/TFE copolymers [ETFE], TFE/HFP/VdF copolymers [THV], VdF/TFE copolymers [VT], polyvinylidene fluoride [PVdF], polychlorotrifluoroethylene [PCTFE], and CTFE/perfluoro(alkyl vinyl ether)/TFE copolymers [CPT]. The fluoropolymer is more preferably a melt-processable fluoropolymer, and still more preferably at least one selected from the group consisting of ETFE, FEP, and PFA.

In the ETFE, the molar ratio of Et unit:TFE unit is preferably 20:80 to 80:20. The molar ratio of Et unit:TFE unit is more preferably 35:65 to 55:45. ETFE is a copolymer including a polymerization unit derived from TFE and a polymerization unit derived from Et, and may include a polymerization unit derived from another fluoromonomer or another non-fluorinated monomer.

Such an additional fluoromonomer and non-fluorinated monomer may be monomers capable of being added to both Et and TFE. A C3-C10 fluorine-containing vinyl monomer is easy to use, and specifically, for example, hexafluoroisobutylene, $CH_2=CFC_3F_6H$, or HFP may be used. In particular, a fluorine-containing vinyl monomer represented by the formula (3):

$$CH_2=CH-Rf^4 \qquad (3)$$

wherein $Rf^4$ represents a C4-C8 perfluoroalkyl group, is one preferred embodiment. The non-fluorinated monomer may be a vinyl monomer represented by the formula (4):

$$CH_2=CH-R^4 \qquad (4)$$

wherein the number of carbon atoms in $R^4$ is not particularly limited, $R^4$ may contain an aromatic ring, and may contain a carbonyl group, an ester group, an ether group, an amide group, a cyano group, a hydroxyl group, or an epoxy group, and $R^4$ contains no fluorine atom.

It is also one preferred embodiment that ETFE is also a Et/TFE/HFP copolymer [EFEP], and may further contain a polymerization unit derived from another fluoromonomer (excluding HFP) or another non-fluorinated monomer. Such an additional fluoromonomer or non-fluorinated monomer is preferably 10 mol % or less and more preferably 5 mol % or less of the entire polymer. The molar ratio of Et unit:TFE unit:monomer unit derived from the at least one monomer selected from the group consisting of other fluoromonomers and other non-fluorinated monomers is preferably 31.5 to 54.7:40.5 to 64.7:0.5 to 10.

The FEP contains a HFP unit in an amount of preferably more than 2% by mass and 20% by mass or less, and more preferably 8% to 15% by mass.

The perfluoro(alkyl vinyl ether) of the PFA is preferably one containing a C1-C6 alkyl group, and more preferably perfluoro(methyl vinyl ether), perfluoro(ethyl vinyl ether), or perfluoro(propyl vinyl ether). The PFA contains a perfluoro(alkyl vinyl ether) unit in an amount of preferably more than 2% by mass and 15% by mass or less, and more preferably 2.5% to 8.0% by mass.

The FEP or PFA each may be polymerized with other monomers as long as they have the above compositions. As other monomers, for example, perfluoro(alkyl vinyl ether) may be used in the case of FEP, and HFP may be used in the case of PFA. Each of other monomers may be used alone, or two or more of these may be used.

The amount of the other monomers to be polymerized with the FEP or PFA depends on the type of the other monomers, and is usually preferably not more than 2% by mass and more preferably not more than 1.5% by mass of the resulting fluoropolymer.

The amounts of the monomer units of the above copolymers can be calculated by appropriately combining any of NMR, FT-IR, elementary analysis, and X-ray fluorescence analysis depending on the types of monomers.

The wet fluoropolymer is produced by suspension polymerization, solution polymerization, or bulk polymerization of the fluoromonomer in the presence of at least the fluorine-containing ether in the present invention. Such a polymerization reaction allows to synthesize a fluoropolymer wet with a solvent such as a solvent containing at least the fluorine-containing ether in the present invention. That is, the wet fluoropolymer including a fluoropolymer and a solvent is produced in a reaction vessel by such a polymerization reaction. After the production step, the wet fluoropolymer contained in the reaction vessel may be directly subjected to the below described vaporizing and discharging step. Alternatively, after the production step, the wet fluoropolymer is transferred from the reaction vessel to a different container, and then may be subjected to the vaporizing and discharging step. Such an embodiment is also within the scope of the present invention. For example, it is also one preferred embodiment that the vaporizing and discharging step is performed after the contents in a reaction vessel are transferred to a different closed container, such as so called a decanter.

The different container is not limited to a specific closed container. Specifically, a container or a container provided in equipment, available for the vaporizing and discharging step can be used in the present invention.

Further, after the production step, the solvent of the wet fluoropolymer contained in the reaction vessel or the different container may be partly or entirely replaced with other solvents as long as the wet fluoropolymer contains the fluorine-containing ether in the present invention.

The different container may be any container available for vaporizing the fluorine-containing ether, and may be a container provided in equipment such as a dryer (e.g. centrifugal thin-film dryer, conical ribbon dryer, container-rotating dryer, Nauta Mixer, PV mixer, spray dryer). The different container is made of glass, stainless steel, or another corrosion-resistant material, and may include a stirrer, a jacket for temperature control, a thermometer, or a cyclone, if necessary.

The polymerization reaction may be initiated in such a way that a reaction vessel is charged with the fluorine-containing ether, a fluoromonomer, and if necessary, an additive, the contents in the reaction vessel are stirred, the reaction vessel is maintained at a predetermined polymerization temperature, and a predetermined amount of a polymerization initiator is fed to initiate a polymerization reaction. A polymerization solvent other than the fluorine-containing ether, a surfactant, a chain transfer agent, or a radical capture agent may be fed. The polymerization may be carried out by batch type polymerization, semi-batch type polymerization, or in a continuous manner. The raw materials for the polymerization reaction may be fed after the start of the polymerization reaction in an intermittent manner or a continuous manner.

The polymerization solvent other than the fluorine-containing ether may be any solvent, and examples thereof include water; fluorine-free organic solvents such as alcohol, ether, and ketone; and fluorine-containing organic solvents having a boiling point of not higher than 100° C. For example, a fluorine-containing organic solvent such as C318 can be used in suspension polymerization.

The polymerization initiator to be used may be a commonly used oil-soluble polymerization initiator and/or water soluble polymerization initiator. Further, the polymerization initiator may be a redox initiator in combination with a reducing agent or the like to initiate the polymerization. The concentration of the polymerization initiator is appropriately determined depending on the type of monomers, the molecular weight of a target fluoropolymer, or the reaction rate.

The fluorine-containing ether in which the polymerization initiator is dissolved may be fed to a reaction vessel.

Examples of the chain transfer agent to be used include hydrocarbons such as isopentane, n-pentane, n-hexane, and cyclohexane; alcohols such as methanol and ethanol; and halogenated hydrocarbons such as carbon tetrachloride, chloroform, methylene chloride, and methyl chloride.

The polymerization temperature of the polymerization reaction is not particularly limited, and is preferably 0° C. to 100° C., and more preferably 10° C. to 90° C. The polymerization pressure is not particularly limited, and is preferably 0.1 to 10 MPa, and more preferably at 0.3 to 5 MPa.

The polymerization temperature indicates the temperature of the solvent in the reaction vessel, and the polymerization pressure indicates the pressure in the reaction vessel.

The method for recovering of the present invention includes vaporizing and discharging vaporizable substances including the fluorine-containing ether by heating the wet fluoropolymer in a container.

The container may be the reaction vessel that has been used for the polymerization reaction of the fluoromonomer, or a different container such as a container having a vaporizing means or a container provided in equipment. The different container to be used may be, for example, selected from the containers listed above. Specifically, the vaporizable substances may be vaporized in the reaction vessel that has been used for the polymerization reaction of the fluoromonomer, or the wet fluoropolymer produced in the reaction vessel is transferred to a different container, and then the vaporizable substances may be vaporized in the different container.

The method of vaporizing the vaporizable substances in the different container after the wet fluoropolymer is transferred thereto may be performed in such a way that, for example, the vaporizable substances are vaporized from the wet fluoropolymer after the wet fluoropolymer is transferred to a container having a vaporizing means or a container provided in equipment. Such an embodiment is also one preferred embodiment of the present invention. In addition, the following embodiment is also one preferred embodiment of the present invention: the wet fluoropolymer is transferred to an equipment such as a centrifugal thin film dryer or the like, and subjected to solid-liquid separation using centrifugal force to reduce the amount of liquid contained in the wet fluoropolymer, and the vaporizable substances are vaporized from the wet fluoropolymer in a container after the wet fluoropolymer is transferred to the container, or in the container provided in the equipment that has been used for the solid-liquid separation.

Such a vaporizing step allows separation of the fluorine-containing ether from compound species contained in the wet fluoropolymer such as a fluoropolymer and solvents.

The "vaporizable substances" used herein may include, in addition to a simple substance of a fluorine-containing ether, a mixture containing substances that are present in the container for the vaporizing step and capable of vaporizing under the conditions where the fluorine-containing ether can vaporize, such as gases, liquefied gases, and solvents. The vaporizable substances vaporized in the vaporizing step may be partly liquefied during their transfer to a cooling means.

The substances capable of vaporizing under the conditions where the fluorine-containing ether can vaporize are determined depending on the type of the fluorine-containing ether used in the polymerization reaction and the types of compound species, contained in the wet fluoropolymer or in a container for the vaporizing step. Specifically, the substances are compounds that have been used in the polymerization reaction, have a boiling point lower than or similar to that of the fluorine-containing ether used in the polymerization reaction, and vaporize under the heating conditions for heating the wet fluoropolymer in a container to vaporize the fluorine-containing ether. Specific examples of such substances include unreacted fluoromonomers, non-fluorinated monomers, the above described polymerization solvents, initiator solvents, chain transfer agents, stabilizers, and water vapor.

In particular, in the system for synthesizing FEP using HFP and TFE as monomers, specific examples of the substances capable of vaporizing include HFP, TFE, polymerization solvents, initiator solvents, chain transfer agents, other copolymerizable fluoromonomers, other copolymerizable non-fluorinated monomers, stabilizers, and water vapor. In the system for synthesizing ETFE using TFE, ethylene, and (perfluorobutyl)ethylene as monomers, specific examples of the substances capable of vaporizing include TFE, ethylene, HFP, polymerization solvents, initiator solvents, chain transfer agents, other copolymerizable fluoromonomers, other copolymerizable non-fluorinated monomers, stabilizers, and water vapor.

Heating in the vaporizing step can be performed by heating a container using a heating means. The heating means may be any means, and may be a hot water bath, an oil bath, or steam heating.

The heating temperature in the vaporizing step may be appropriately set at a temperature at which the fluorine-containing ether vaporizes, but the fluoropolymer does not decompose or vaporize, depending on the type of the synthesized fluoropolymer and the type of the fluorine-containing ether. For example, the container may be heated such that the temperature in the container is within the range of 0° C. to 200° C. A heating temperature higher than 200° C. causes adverse effects, for example, the fluoropolymer is stained. The heating temperature is more preferably 0° C. to 100° C., still more preferably 20° C. to 90° C., and particularly preferably 40° C. to 90° C.

The vaporizing step may be performed in any manner. For example, the vaporizable substances may be vaporized by reducing the pressure in the container containing the wet fluoropolymer to lower than atmospheric pressure. When the vaporizable substances are vaporized by reducing the pressure in the container to lower than atmospheric pressure in this manner, the recovery time can be further shortened, and the heating temperature can be lowered. Therefore, the fluorine-containing ether can be more easily separated from the fluoropolymer, water, and the like.

The vaporizing step may be performed while the wet fluoropolymer in the container is stirred. When the vaporizable substances are vaporized while the wet fluoropolymer in the container is stirred in this manner, the fluorine-containing ether can be easily separated from the fluoropolymer, water, and the like.

The stirring rate of the wet fluoropolymer may be appropriately set in light of the size of the container, the concentration of the wet fluoropolymer, the vaporization rate of the vaporizable substances including a target fluorine-containing ether, and the like. For example, the stirring rate is preferably 10 to 600 rpm, more preferably 30 to 300 rpm, and still more preferably 50 to 250 rpm.

In the vaporizing step, a fluorine-containing compound having a boiling point lower than that of the fluorine-containing ether may be added to the wet fluoropolymer. In particular, in cases where the weight of the fluorine-containing ether contained in the container for the vaporizing step is insufficient relative to the weight of the fluoropolymer, a fluorine-containing compound having a boiling point lower than that of the fluorine-containing ether is preferably added to the wet fluoropolymer. Such a vaporizing step including adding a fluorine-containing compound having a boiling point lower than that of the fluorine-containing ether to the wet fluoropolymer allows easy separation of the fluorine-containing ether from the fluoropolymer, and promotion of vaporization of the fluorine-containing ether. As a result, the amount of the fluorine-containing ether left in the wet fluoropolymer can be reduced to further increase the recovery yield of the fluorine-containing ether. In view of this, the fluorine-containing compound, which is to be added to the wet fluoropolymer, having a boiling point lower than that of the fluorine-containing ether herein is also referred to as a "vaporization promoting substance".

The vaporization promoting substance is preferably one highly compatible with a fluoropolymer, and is therefore appropriately selected depending on the type of a fluoropolymer to be produced. Preferred examples of the vaporization promoting substance to be used include hexafluoropropylene (HFP) and perfluorocyclobutane (C318).

Each of these vaporization promoting substances may be used alone, or two or more of these may be used in combination.

Examples of the embodiments of adding the vaporization promoting substance to the wet fluoropolymer include an embodiment in which FEP is synthesized as a fluoropolymer and HFP is added as a vaporization promoting substance, and an embodiment in which ETFE is synthesized as a fluoropolymer and C318 is added as a vaporization promoting substance.

The amount of the vaporization promoting substance is not particularly limited, and is preferably 1% to 10000% by mass based on 100% by mass of the fluorine-containing ether when the amount of the fluorine-containing ether contained in the wet fluoropolymer at the time of addition of the vaporization promoting substance is 100% by mass. Addition of the above-described amount of the vaporization promoting substance can sufficiently enhance the effects obtained by adding the vaporization promoting substance, thereby increasing the recovery yield of the fluorine-containing ether.

The method for recovering of the present invention includes transferring the vaporizable substances vaporized in the vaporizing and discharging step to a cooling means to cool the vaporizable substances. The vaporizable substances in the vaporized state transferred to a cooling means are cooled to be liquefied to give vaporizable substances in the liquid state including the fluorine-containing ether.

The cooling temperature in the cooling step may be appropriately set to a temperature at which the fluorine-containing ether contained in the vaporizable substances in the vaporized state is liquefied. For example, cooling is performed such that the temperature in the cooling means is set within the range of preferably −30° C. to 20° C., and more preferably 0° C. to 20° C.

The cooling means in the cooling step may be any means, and is preferably a condenser. Thus, it is one preferred embodiment of the present invention that the cooling means in the cooling step is a condenser.

The method for recovering of the present invention preferably includes transferring the vaporizable substances liquefied by cooling in the cooling step to a distillation means to distill the vaporizable substances. The fluorine-containing ether can be separated from other compounds contained in the vaporizable substances by subjecting the vaporizable substances liquefied in the cooling step to such distillation. Thus, the fluorine-contained ether can be separated and recovered.

The distillation means in the distillation step may be any means, and may be, for example, distillation equipment or multistage distillation equipment (rectification equipment).

The method for recovering of the present invention may include, if necessary, transferring the vaporizable substances vaporized in the vaporizing step to a compression means to compress the vaporizable substances. Compression of the vaporizable substances in the vaporized state allows an increase in the gas concentration, which leads to a further increase in the recovery yield of the fluorine-containing ether. In the case of performing the compression step in the method for recovering of the present invention as described above, it is preferred that the vaporizable substances vaporized in the vaporizing step is at first transferred to the compression means and compressed, and the vaporizable substances compressed in the compression step are then transferred to the cooling means and cooled. That is, the compression step is preferably performed between the vaporizing and discharging step, and the cooling step.

The upper limit of the compression ratio in the compression step is not particularly limited, and is for example, preferably 2 to 40. Such a compression ratio within the above range is enough to sufficiently compress the vaporizable substances in the vaporized state, and contributes to a further increase in the recovery yield of the fluorine-containing ether.

The compression means in the compression step may be any means, and may be, for example, a centrifugal compressor, an axial flow compressor, or a displacement compressor. Among these, a displacement compressor is particularly preferred. That is, it is one preferred embodiment of the present invention that the compression means in the compression step is a compressor.

In cases where the compression means is a compressor, the vaporizable substances in the vaporized state transferred to the compressor are preferably heated again before being compressed because the vaporizable substances in the liquid state may cause a failure of the compressor if the vaporizable substances in the vaporized state transferred to a compressor are liquefied before being compressed by the compressor.

In the method for recovering of the present invention, the vaporizable substances liquefied by cooling in the cooling step, or the fluorine-containing ether separated in the distillation step in the case of performing the distillation step are/is transferred to a recovery container and recovered. It is also one preferred embodiment of the present invention that the method for recovering includes transferring the vaporizable substances liquefied by cooling in the cooling step, or in the case of performing the distillation step, the fluorine-containing ether separated in the distillation step to a recovery container to recover them.

In the present invention, for example, the recovery container to recover the vaporizable substances in the liquid state may include a cooling means, and the cooling step and the recovery step of the vaporizable substances may be performed at the same time. That is, it is also one preferred embodiment of the present invention that the cooling step and the recovery step of the vaporizable substances include transferring the vaporizable substances vaporized in the vaporizing step to a recovery container including a cooling means, and recovering the vaporizable substances liquefied by cooling in the recovery container.

Furthermore, the vaporizable substances in the liquid state recovered in the recovery container may be transferred to the distillation means, and distilled. Thereby, the fluorine-containing ether can be separated and recovered.

The fluorine-containing ether separated and recovered from the wet fluoropolymer can be reused.

In the method for recovering of the present invention, a value of x/V is preferably at most 0.140, wherein V represents the inner volume (L) of the container, and x represents the discharge rate (kg/hour) of the vaporizable substances from the container.

When the vaporizable substances in the vaporized state are transferred from the container for the vaporizing step to the cooling means at such a transfer rate, the vaporizable substances containing the fluorine-containing ether can be transferred from the container for the vaporizing step to the cooling means without bringing the fluoropolymer together therewith, and the fluoropolymer is prevented from being mixed into the vaporizable substances. In this manner, a decrease in the yield of the fluoropolymer can be prevented. Mixing of the fluoropolymer into the vaporizable substances is remarkably disadvantageous in separation of the fluorine-containing ether from the vaporizable substances and purification of the fluorine-containing ether, or reuse of the fluorine-containing ether. If the vaporizable substances are transferred too rapidly, the fluoropolymer may be transferred along with the vaporizable substances to be mixed into the vaporizable substances when the vaporizable substances are transferred from the container for the vaporizing step to the cooling means. On the other hand, if the vaporizable substances are transferred too slowly, the resulting fluoropolymer may be stained. For the transfer rate of the vaporizable substances, the x/V value is more preferably 0.0012 to 0.090, and the x/V value is still more preferably 0.0060 to 0.050.

The discharge rate (x) of the vaporizable substances from the container for the vaporizing step is not particularly limited, and can be controlled by, for example, adjusting the opening degree of a valve during their transfer, arranging an orifice in a pipe, or reducing the size of a pipe. For example, it is one preferred method that a needle valve is automatically controlled in accordance with the discharge rate of the vaporizable substances in the vaporized state.

The method for recovering of the present invention can provide a fluoropolymer obtained by drying a fluoropolymer left in the container after the vaporizing step (hereinafter also referred to simply as "dried fluoropolymer") in an amount of 0.01 to 0.4 kg per liter of the volume of the container. The amount of the dry fluoropolymer obtained is not particularly limited.

In the method for recovering of the present invention, a commonly used pipe can be used to transfer the vaporizable substances in the vaporized state, the vaporizable substances in the liquefied state, or the fluorine-containing ether separated. The vaporizable substances in the vaporized state are sometimes partly liquefied in the pipe during their transfer to a cooling means.

In the method for recovering of the present invention, the vaporizable substances are vaporized from the wet fluoropolymer, cooled, and liquefied, and then the vaporizable substances in the liquid state are recovered. If necessary, the vaporizable substances in the liquid state are purified by distillation to give a fluorine-containing ether. The resulting fluorine-containing ether is reused. As the recovery step of the vaporizable substances progresses, the pressure in the container reduces. The recovery step may preferably be stopped at the time when the pressure in the container is reduced to −0.001 to −0.09 MPa, but in the present invention, the pressure in the container at which the recovery step is stopped is not limited to atmospheric pressure or lower.

The fluoropolymer synthesized in the production step can be collected after it is separated from the vaporizable substances including the fluorine-containing ether by vaporizing and discharging the vaporizable substances by heating the wet fluoropolymer in the container in the method for recovering of the present invention. In cases where an aqueous dispersion containing the fluoropolymer is obtained through a polymerization reaction in the production step, the fluoropolymer in the aqueous dispersion may be precipitated, washed, and dried to collect a dry fluoropolymer. In cases where the fluoropolymer is obtained in the form of slurry through a polymerization reaction, a slurry may be withdrawn from a reaction vessel, washed, and dried to collect a dry fluoropolymer. The drying provides the fluoropolymer in the form of powder.

One example of the preferred embodiments of the method for recovering of the present invention is a method including the steps of: producing a wet fluoropolymer by suspension polymerization, solution polymerization, or bulk polymerization in the presence of at least a fluorine-containing ether represented by the formula (1):

$$Rf\text{—}O\text{—}R \qquad (1)$$

wherein Rf represents a C2-C6 fluoroalkyl group or a C2-C6 alkyl group, and R represents a C1-C4 fluoroalkyl group or a C1-C4 alkyl group, provided that the total number of carbon atoms in Rf and R is at most 8; vaporizing and discharging vaporizable substances including the fluorine-containing ether by heating the wet fluoropolymer in a container; transferring the vaporizable substances in the vaporized state to a recovery container equipped with a cooling means; recovering the vaporizable substances liquefied by cooling in the recovery container; subsequently adding the vaporization promoting substance to the wet fluoropolymer in the container; performing the steps of from vaporizing to recovering; and further repeating the steps of from adding the vaporization promoting substance to recovering once or more; after completion of the final recovery step, returning the pressure in the container to atmospheric pressure; and washing and drying the wet fluoropolymer remained in the container to give a dry fluoropolymer. The method for recovering may further include the steps of: transferring the vaporizable substances in the liquefied state recovered in the recovery container to a distillation means to distill the vaporizable substances to separate and recover the fluorine-containing ether. In such an embodiment, the steps of from adding the vaporization promoting substance to recovering the vaporizable substances are repeated preferably three or more times, more preferably five or more times, and still more preferably seven or more times.

Figure 1:
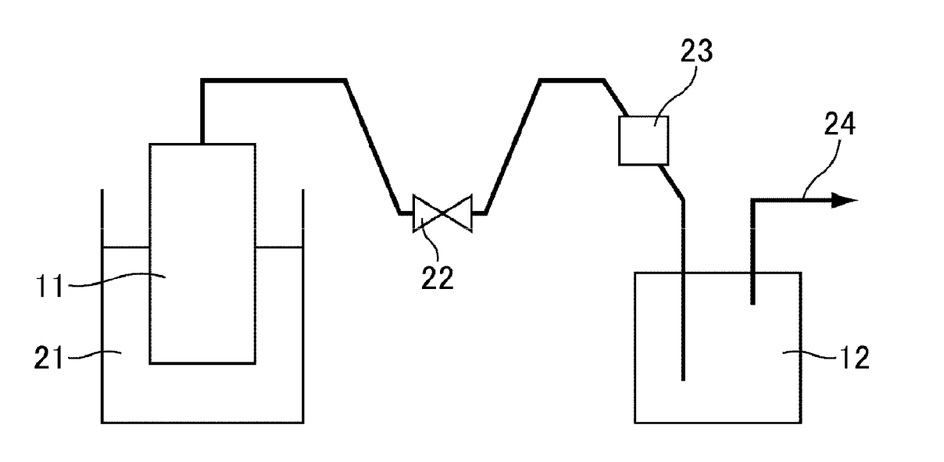
FIG. 1 is a flow diagram illustrating an example of the overall process of the method for recovering of the present invention.

An example of the overall process of the method for recovering of the present invention is described using a flow diagram in FIG. 1.

First, raw materials for a polymerization reaction including a fluorine-containing ether represented by the formula (1) are placed in a reaction vessel 11, and polymerization of the materials is performed to synthesize a wet fluoropolymer (production step of wet fluoropolymer). Vaporizable substances including the fluorine-containing ether are vaporized and discharged by heating the synthesized wet fluoropolymer with a heating means 21 (vaporizing and discharging step). Then, the vaporizable substances in the vaporized state are transferred to a cooling means 23 such as a condenser, and cooled (cooling step). The vaporizable substances liquefied by cooling are transferred to a recovery container 12 and recovered (recovery step). The transfer rate of the vaporizable substances including the fluorine-containing ether from the reaction vessel 11 to the cooling means 23 is adjusted, for example, by adjusting the opening degree of a valve 22 to control the discharge rate of the vaporizable substances.

In the present invention, step(s) other than these steps may be included, and each step may be repeated twice or more, as long as the effects of the present invention are achieved. In cases where each step is repeated twice or more, at least one of the repeated steps needs to satisfy the present invention. Further, in cases where a series of steps from the vaporizing and discharging step to the recovery step is repeated several times, at least one series of the steps preferably satisfies a value of x/V of at most 0.140 V, wherein V represents the inner volume (L) of the container, and x represents the discharge rate (kg/hour) of the vaporizable substances discharged from the container. The value of x/V is more preferably 0.0012 to 0.090, and still more preferably 0.0060 to 0.050.

EXAMPLE

The present invention is explained by means of examples, but is not limited thereto.

The values in the examples were measured by the following methods.

[Melting Point]

Using a differential scanning calorimeter (DSC) (trade name: RDC 220, produced by Seiko Instruments Inc.), 3 mg of a sample was heated from room temperature to 300° C. at 10° C./min, cooled down to room temperature at −10° C./min, and heated again from room temperature at 10° C./min. The melting peak temperature in this case was determined as the melting point.

[MFR]

Using a melt indexer (produced by Toyo Seiki Seisakusho, Ltd.), the mass (g/10 minutes) of the polymer flowing out through a nozzle with a 2-mm inner diameter and an 8-mm length during a 10-minute period of time under a load of 5 kg was determined as a MFR, in accordance with ASTM D3307-01.

Comparative Example 1

(Polymerization Reaction)

A 175-L autoclave was charged with 40 L of distilled water, and sufficiently purged with nitrogen. Subsequently, 40 kg of hexafluoropropylene (HFP) was fed. The temperature in the system was maintained at 29° C., and the stirring rate was maintained at 235 rpm. Then, 4 kg of tetrafluoroethylene (TFE) and 200 g of methanol were fed, and thereafter 100 g of a 8% by weight solution of 7H-dodecafluoroheptanoyl peroxide/perfluorohexane (PFH) was fed thereto to initiate polymerization. Then, 100 g of a 8% by weight solution of 7H-dodecafluoroheptanoyl peroxide/perfluorohexane was fed every 2 hours 11 times over the course of the polymerization. Because the pressure in the system drops with the progress of the polymerization, tetrafluoroethylene (TFE) was continuously fed to maintain the pressure in the system at 0.94 MPa. The amount of the tetrafluoroethylene (TFE) fed was 40 kg in total. The stirring was continued for 24 hours, and the reaction was stopped.

(Solvent Recovery Step)

The temperature in the autoclave was set at 80° C., and the temperature in a recovery tank was set at 10° C. Gas components were transferred to the recovery tank from the gas phase portion in the autoclave using a compressor at a rate of about 5 kg/hour by adjusting the opening degree of a valve in this process. The pressure in the autoclave was reduced to −0.02 MPa over 8 hours.

Next, 500 g of HFP was fed to the autoclave, and the contents in the autoclave were mixed for 30 minutes. The pressure in the autoclave was reduced to −0.02 MPa at a rate of about 1.3 kg/hour over 30 minutes by adjusting the opening degree of a valve in this step.

The steps of feeding HFP through reducing the pressure to −0.02 MPa in the recovery operation were repeated seven times, and thereafter the pressure was returned to atmospheric pressure. The reaction product was washed with water.

An amount of 883 g of the perfluorohexane was recovered as a mixture with HFP and TFE in the recovery tank from 1104 g of the perfluorohexane fed for the polymerization. The recovery yield was 80%. The amount of fluororesin powder mixed into the recovered liquid along with the gas components was less than 0.001 kg.

The pressure in the autoclave was released to atmospheric pressure, and then the contents were dried to give 45 kg of a fluororesin (TFE/HFP copolymer) as a white powder. The resulting fluororesin had a melting point of 266° C. and a MFR measured at 372° C. of 5.0. The compression ratio of the compressor was 7.5. The perfluorohexane, HFP, and TFE recovered in the recovery tank were transferred to a rectifier (multistage distillation column) made of SUS, and they were rectified (subjected to multistage distillation) to separate the perfluorohexane from HFP and TFE which had a boiling point lower than that of the perfluorohexane. The perfluorohexane separated from HFP and TFE was further subjected to distillation using a simple distillation apparatus.

Comparative Example 2

A polymerization reaction and a solvent recovery step were performed as in Comparative Example 1, except that in the polymerization reaction, a 8% by weight solution of 7H-dodecafluoroheptanoyl peroxide/CFC113 (1,1,2-trichloro-1,2,2-trifluoroethane) was used instead of a 8% by weight solution of 7H-dodecafluoroheptanoyl peroxide/perfluorohexane. The recovery yield of CFC113 recovered as a mixture with HFP and TFE in the recovery tank was 80%. The amount of fluororesin powder mixed into the recovered liquid along with the gas components was less than 0.001 kg. The amount of fluororesin powder obtained was 44 kg. The fluororesin had a melting point of 268° C., and a MFR of 2.0.

CFC113, HFP, and TFE recovered in the recovery tank were transferred to a rectifier (multistage distillation column) made of SUS, and they were rectified (subjected to multistage distillation) to separate CFC113 from HFP and TFE which had a boiling point lower than that of CFC113. CFC113 separated from HFP and TFE was further subjected to distillation using a simple distillation apparatus.

Comparative Example 3

(Polymerization Reaction)

A polymerization reaction was performed as in Comparative Example 1.

(Solvent Recovery Step)

A solvent recovery step was performed as in Comparative Example 1, except that the feeding of HFP in the recovery operation was not performed.

The recovery yield of the perfluorohexane recovered as a mixture with HFP and TFE in the recovery tank was 65%. The amount of fluororesin powder mixed into the recovered liquid along with the gas components was less than 0.001 kg.

Example 1

(Polymerization Reaction)

A polymerization reaction was performed as in Comparative Example 1, except that a 8% by weight solution of 7H-dodecafluoroheptanoyl peroxide/$C_4F_9OCH_3$ (HFE7100) was used instead of a 8% by weight solution of 7H-dodecafluoroheptanoyl peroxide/perfluorohexane.

(Solvent Recovery Step)

The temperature in the autoclave was set at 80° C., and the temperature in a recovery tank was set at 10° C. Gas components were transferred to the recovery tank from the gas phase portion in the autoclave using a compressor at a rate of about 5 kg/hour by adjusting the opening degree of a valve in this step. The pressure in the autoclave was reduced to −0.02 MPa over 8 hours.

Next, 500 g of HFP was fed to the autoclave, and the contents in the autoclave were mixed for 30 minutes. The pressure in the autoclave was reduced to −0.02 MPa at a rate of about 1.3 kg/hour over 30 minutes by adjusting the opening degree of a valve in this step.

The steps of feeding HFP through reducing the pressure to −0.02 MPa in the recovery operation were repeated seven times, and thereafter the pressure was returned to atmospheric pressure. The reaction product was washed with water.

An amount of 1093 g of $C_4F_9OCH_3$ was recovered as a mixture with HFP and TFE in the recovery tank from 1104 g of $C_4F_9OCH_3$ fed for the polymerization. The recovery yield was 99%. The amount of fluororesin powder mixed into the recovered liquid along with the gas components was less than 0.001 kg.

The pressure in the autoclave was released to atmospheric pressure, and then the contents were dried to give 45 kg of a fluororesin (TFE/HFP copolymer) as a white powder. The resulting fluororesin had a melting point of 265° C., and a MFR of 5.5. The compression ratio of the compressor was 7.5.

$C_4F_9OCH_3$, HFP, and TFE recovered in the recovery tank were transferred to a rectifier (multistage distillation column) made of SUS, and they were rectified (subjected to multistage distillation) to separate $C_4F_9OCH_3$ from HFP and TFE which had a boiling point lower than that of $C_4F_9OCH_3$. $C_4F_9OCH_3$ separated from HFP and TFE was subjected to distillation using a simple distillation apparatus.

Example 2

(Polymerization Reaction)
A polymerization reaction was performed as in Example 1.
(Solvent Recovery Step)
The temperature in the autoclave was set at 80° C., and the temperature in a recovery tank was set at 10° C. Gas components were transferred to the recovery tank from the gas phase portion in the autoclave using a compressor at a rate of about 1.5 kg/hour by adjusting the opening degree of a valve in this step. The pressure in the autoclave was reduced to −0.02 MPa over 27 hours.

Next, 500 g of HFP was fed to the autoclave, and the contents in the autoclave were mixed for 30 minutes. The pressure in the autoclave was reduced to −0.02 MPa at a rate of about 1.5 kg/hour over 26 minutes by adjusting the opening degree of a valve in this step.

The steps of feeding HFP through reducing the pressure to −0.02 MPa in the recovery operation were repeated seven times, and thereafter the pressure was returned to atmospheric pressure. The reaction product was washed with water.

An amount of 1093 g of $C_4F_9OCH_3$ was recovered as a mixture with HFP and TFE in the recovery tank from 1104 g of $C_4F_9OCH_3$ fed for the polymerization. The recovery yield was 99%. The amount of fluororesin powder mixed into the recovered liquid along with the gas components was less than 0.001 kg. The pressure in the autoclave was released to atmospheric pressure, and then the contents were dried to give 47 kg of a fluororesin (TFE/HFP copolymer) as a white powder. The resulting fluororesin had a melting point of 265° C., and a MFR of 5.5. The compression ratio of the compressor was 7.5.

$C_4F_9OCH_3$, HFP, and TFE recovered in the recovery tank were transferred to a rectifier (multistage distillation column) made of SUS, and they were rectified (subjected to multistage distillation) to separate $C_4F_9OCH_3$ from HFP and TFE which had a boiling point lower than that of $C_4F_9OCH_3$. Further, $C_4F_9OCH_3$ separated from HFP and TFE was subjected to distillation using a simple distillation apparatus.

Example 3

(Polymerization Reaction)
A polymerization reaction was performed as in Example 1.
(Solvent Recovery Step)
A solvent recovery step was performed as in Example 1, except that feeding of HFP in the recovery operation was not performed.

The recovery yield of $C_4F_9OCH_3$ recovered as a mixture with HFP and TFE in the recovery tank was 90%. The amount of fluororesin powder mixed into the recovered liquid along with the gas components was less than 0.001 kg.

Example 4

(Polymerization Reaction)
A polymerization reaction was performed as in Example 1.
(Solvent Recovery Step)
A solvent recovery step was performed as in Example 3, except that gas components were transferred to the recovery tank from the gas phase portion in the autoclave at a rate of about 8.5 kg/hour over 4.7 hours by adjusting the opening degree of a valve in this step.

The recovery yield of $C_4F_9OCH_3$ recovered as a mixture with HFP and TFE in the recovery tank was 90%. The amount of fluororesin powder mixed into the recovered liquid along with the gas components was less than 0.001 kg.

Example 5

(Polymerization Reaction)
A polymerization reaction was performed as in Example 1.
(Solvent Recovery Step)
A solvent recovery step was performed as in Example 3, except that gas components were transferred to the recovery tank from the gas phase portion in the autoclave at a rate of about 15.5 kg/hour over 2.6 hours by adjusting the opening degree of a valve in this step.

The recovery yield of $C_4F_9OCH_3$ recovered as a mixture with HFP and TFE in the recovery tank was 90%. The fluororesin transferred along with the gas components was present in the recovered liquid in an amount equivalent to 0.01 kg of fluororesin powder.

Example 6

(Polymerization Reaction)
A polymerization reaction was performed as in Example 1.
(Solvent Recovery Step)
A solvent recovery step was performed as in Example 3, except that gas components were transferred to the recovery tank from the gas phase portion in the autoclave at a rate of about 22 kg/hour over 1.8 hours by adjusting the opening degree of a valve in this step.

The recovery yield of $C_4F_9OCH_3$ recovered as a mixture with HFP and TFE in the recovery tank was 90%. The fluororesin transferred along with the gas components was present in the recovered liquid in an amount equivalent to 0.03 kg of fluororesin powder.

Example 7

(Polymerization Reaction)

A polymerization reaction was performed as in Example 1.

(Solvent Recovery Step)

The temperature in the autoclave was set at 80° C., and the temperature in a recovery tank was set at 10° C. Gas components were transferred to the recovery tank from the gas phase portion in the autoclave using a compressor at a rate of about 25 kg/hour by adjusting the opening degree of a valve in this step. The fluororesin was transferred along with the gas components to be mixed in the recovered liquid in an amount equivalent to 5 kg of fluororesin powder. The recovery yield of $C_4F_9OCH_3$ was 90%. The compression ratio of the compressor was 7.5.

Example 8

(Polymerization Reaction)

A polymerization reaction was performed as in Example 1.

(Solvent Recovery Step)

The temperature in the autoclave was set at 80° C., and the temperature in a recovery tank was set at 10° C. Gas components were transferred to the recovery tank from the gas phase portion in the autoclave using a compressor at a rate of about 1 kg/hour by adjusting the opening degree of a valve in this step. The pressure in the autoclave was reduced to −0.02 MPa over 40 hours.

Next, 500 g of HFP was fed to the autoclave, and the contents in the autoclave were mixed for 30 minutes. The pressure in the autoclave was reduced to −0.02 MPa at a rate of about 0.2 kg/hour over 3.5 hours by adjusting the opening degree of a valve in this step.

The steps of feeding HFP through reducing the pressure to −0.02 MPa in the recovery operation were repeated seven times, and thereafter the pressure was returned to atmospheric pressure. The reaction product was washed with water.

An amount of 1093 g of $C_4F_9OCH_3$ was recovered as a mixture with HFP and TFE in the recovery tank from 1104 g of $C_4F_9OCH_3$ fed for the polymerization. The recovery yield was 99%. The amount of fluororesin powder mixed into the recovered liquid along with the gas components was less than 0.001 kg.

The pressure in the autoclave was released to atmospheric pressure, and then the contents were dried to give 45 kg of a fluororesin (TFE/HFP copolymer) as a powder. The powder was colored in pale gray. The resulting fluororesin had a melting point of 266° C. and a MFR measured at 372° C. of 4.0. The compression ratio of the compressor was 7.5.

Example 9

(Polymerization Reaction)

A 175-L autoclave was charged with 55 L of distilled water, and sufficiently purged with nitrogen. Subsequently, 38 kg of perfluorocyclobutane (C318) was fed. The temperature in the system was maintained at 35° C., and the stirring rate was maintained at 235 rpm.

Then, 64 g of cyclohexane, 165 g of (perfluorobutyl)ethylene, 240 g of ethylene, and 11 kg of TFE were fed, and thereafter 300 g of a 50% by weight solution of di-n-propyl peroxydicarbonate (NPP)/$C_4F_9OCH_3$ (HFE7100) was fed thereto as a polymerization initiator to initiate polymerization.

As the pressure in the system drops with the progress of the polymerization, a monomer mixture of TFE/ethylene/(perfluorobutyl)ethylene (TFE/ethylene/(perfluorobutyl)ethylene (molar ratio)=50/45/5) was continuously fed to maintain the pressure in the system at 1.25 MPa. The amount of the monomer mixture of TFE/ethylene/(perfluorobutyl)ethylene fed was 50 kg in total. The stirring was continued for 24 hours, and the reaction was stopped.

(Solvent Recovery Step)

The temperature in the autoclave was set at 80° C., and the temperature in a recovery tank was set at 10° C. Gas components were transferred to the recovery tank from the gas phase portion in the autoclave using a compressor at a rate of about 6.3 kg/hour by adjusting the opening degree of a valve in this step. Gas components not liquefied in the cooling step were discharged from the recovery tank through a duct of the recovery tank to a gas holder to regulate the inner pressure of the recovery tank to the range of 0.6 to 0.8 MPa. The pressure in the autoclave was reduced to −0.02 MPa over 8 hours.

Next, 500 g of C318 was fed to the autoclave, and the contents in the autoclave were mixed for 30 minutes. The pressure in the autoclave was reduced to −0.02 MPa at a rate of about 1.1 kg/hour over 30 minutes by adjusting the opening degree of a valve in this step.

The steps of feeding C318 through reducing the pressure to −0.02 MPa in the recovery operation were repeated seven times, and thereafter the pressure was returned to atmospheric pressure. The reaction product was washed with water.

99% of $C_4F_9OCH_3$ fed for the polymerization was recovered as a mixture with C318, TFE, and ethylene in the recovery tank. The amount of fluororesin powder mixed into the recovered liquid along with the gas components was less than 0.001 kg. The amount of fluororesin powder obtained was 39 kg. The fluororesin had a melting point of 245° C., and a MFR of 7.5. The compression ratio of the compressor was 7.5.

$C_4F_9OCH_3$, C318, TFE, and ethylene recovered in the recovery tank were transferred to a rectifier (multistage distillation column) made of SUS, and they were rectified (subjected to multistage distillation) to separate $C_4F_9OCH_3$ from ethylene, TFE, and C318 which had a boiling point lower than that of $C_4F_9OCH_3$. $C_4F_9OCH_3$ separated from ethylene, TFE, and C318 was subjected to distillation using a simple distillation apparatus.

Example 10

(Polymerization Reaction)

A polymerization reaction was performed as in Example 9.

(Solvent Recovery Step)

A solvent recovery step was performed as in Example 9, except that feeding of C318 in the recovery operation was not performed.

The recovery yield of $C_4F_9OCH_3$ recovered as a mixture with C318, TFE, and ethylene in the recovery tank was 90%. The amount of fluororesin powder mixed into the recovered liquid along with the gas components was less than 0.001 kg.

Example 11

(Polymerization Reaction)

A polymerization reaction was performed as in Example 9.

(Solvent Recovery Step)

The temperature in the autoclave was set at 80° C., and the temperature in a recovery tank was set at −20° C. Gas components were transferred to the recovery tank from the gas phase portion in the autoclave at a rate of about 6.3 kg/hour by adjusting the opening degree of a valve in this step without using a compressor. Gas components not liquefied in the cooling step were discharged from the recovery tank through a duct of the recovery tank to a gas holder to regulate the inner pressure of the recovery tank to the range of 0.6 to 0.8 MPa. The pressure in the autoclave was reduced to −0.02 MPa over 8 hours.

Next, 500 g of C318 was fed to the autoclave, and the contents in the autoclave were mixed for 30 minutes. The pressure in the autoclave was reduced to −0.02 MPa at a rate of about 1.1 kg/hour over 30 minutes by adjusting the opening degree of a valve in this step.

The steps of feeding C318 through reducing the pressure to −0.02 MPa in the recovery operation were repeated seven times, and thereafter the pressure was returned to atmospheric pressure. The reaction product was washed with water.

90% of $C_4F_9OCH_3$ fed for the polymerization was recovered as a mixture with C318, TFE, and ethylene in the recovery tank. The amount of fluororesin powder mixed into the recovered liquid along with the gas components was less than 0.001 kg. The amount of fluororesin powder obtained was 39 kg. The fluororesin had a melting point of 245° C., and a MFR of 7.5.

$C_4F_9OCH_3$, C318, TFE, and ethylene recovered in the recovery tank were transferred to a rectifier (multistage distillation column) made of SUS, and they were rectified (subjected to multistage distillation) to separate $C_4F_9OCH_3$ from ethylene, TFE, and C318 which had a boiling point lower than that of $C_4F_9OCH_3$. $C_4F_9OCH_3$ separated from ethylene, TFE, and C318 was subjected to distillation using a simple distillation apparatus.

Example 12

(Polymerization Reaction)

A 175-L autoclave was charged with 55 L of distilled water, and sufficiently purged with nitrogen. Subsequently, 38 kg of $C_4F_9OCH_3$ (HFE7100) was fed. The temperature in the system was maintained at 35° C., and the stirring rate was maintained at 235 rpm.

64 g of cyclohexane, 165 g of (perfluorobutyl)ethylene, 240 g of ethylene, and 11 kg of TFE were fed, and thereafter 300 g of a 50% by weight solution of di-n-propyl peroxydicarbonate (NPP)/$C_4F_9OCH_3$ (HFE7100) was fed thereto as a polymerization initiator to initiate polymerization.

As the pressure in the system drops with the progress of the polymerization, a monomer mixture of TFE/ethylene/(perfluorobutyl)ethylene (TFE/ethylene/(perfluorobutyl)ethylene (molar ratio)=50/45/5) was continuously fed to maintain the pressure in the system at 1.25 MPa. The amount of the monomer mixture of TFE/ethylene/(perfluorobutyl)ethylene fed was 50 kg in total. The polymerization was continued for 24 hours, and the reaction was stopped.

(Solvent Recovery Step)

The temperature in the autoclave was set at 80° C., and the temperature in a recovery tank was set at 10° C. Gas components were transferred to the recovery tank from the gas phase portion in the autoclave using a compressor at a rate of about 6.3 kg/hour by adjusting the opening degree of a valve in this step. Gas components not liquefied in the cooling step were discharged from the recovery tank through a duct of the recovery tank to a gas holder to regulate the inner pressure of the recovery tank to the range of 0.6 to 0.8 MPa. The pressure in the autoclave was reduced to −0.02 MPa over 8 hours, and thereafter returned to atmospheric pressure. The reaction product was washed with water.

99% of $C_4F_9OCH_3$ fed for the polymerization was recovered as a mixture with TFE and ethylene in the recovery tank. The amount of fluororesin powder mixed into the recovered liquid along with the gas components was less than 0.001 kg.

The amount of fluororesin powder obtained was 39 kg. The fluororesin had a melting point of 245° C., and a MFR of 11.3. The compression ratio of the compressor was 7.5.

$C_4F_9OCH_3$, TFE, and ethylene recovered in the recovery tank were transferred to a rectifier (multistage distillation column) made of SUS, and they were rectified (subjected to multistage distillation) to separate $C_4F_9OCH_3$ from ethylene and TFE which had a boiling point lower than that of $C_4F_9OCH_3$. $C_4F_9OCH_3$ separated from ethylene and TFE was subjected to distillation using a simple distillation apparatus.

Example 13

(Polymerization Reaction)

A polymerization reaction was performed as in Example 12, except that $C_3F_7OCH_3$ (HFE7000) was used instead of $C_4F_9OCH_3$ (HFE7100).

(Solvent Recovery Step)

The temperature in the autoclave was set at 80° C., and the temperature in a recovery tank was set at 10° C. Gas components were transferred to the recovery tank from the gas phase portion in the autoclave using a compressor at a rate of about 6.3 kg/hour by adjusting the opening degree of a valve in this step. Gas components not liquefied in the cooling step were discharged from the recovery tank through a duct of the recovery tank to a gas holder to regulate the inner pressure of the recovery tank to the range of 0.6 to 0.8 MPa. The pressure in the autoclave was reduced to −0.02 MPa over 8 hours, and thereafter returned to atmospheric pressure. The reaction product was washed with water. 99% of $C_3F_7OCH_3$ fed for the polymerization was recovered as a mixture with TFE and ethylene in the recovery tank. The amount of fluororesin powder mixed into the recovered liquid along with the gas components was less than 0.001 kg.

The amount of fluororesin powder obtained was 39 kg. The fluororesin had a melting point of 245° C., and a MFR of 11.6. The compression ratio of the compressor was 7.5.

$C_3F_7OCH_3$, TFE, and ethylene recovered in the recovery tank were transferred to a rectifier (multistage distillation column) made of SUS, and they were rectified (subjected to multistage distillation) to separate $C_3F_7OCH_3$ from ethylene and TFE which had a boiling point lower than that of $C_3F_7OCH_3$. $C_3F_7OCH_3$ separated from ethylene and TFE was subjected to distillation using a simple distillation apparatus.

Example 14

(Polymerization Reaction)

A polymerization reaction was performed as in Example 12, except that $CF_3CH_2OCF_2CHF_2$ (HFE-S7) was used instead of $C_4F_9OCH_3$ (HFE7100).

(Solvent Recovery Step)

The temperature in the autoclave was set at 80° C., and the temperature in a recovery tank was set at 10° C. Gas components were transferred to the recovery tank from the gas phase portion in the autoclave using a compressor at a rate of about 6.3 kg/hour by adjusting the opening degree of a valve in this step. Gas components not liquefied in the cooling step were discharged from the recovery tank through a duct of the recovery tank to a gas holder to regulate the inner pressure of the recovery tank to the range of 0.6 to 0.8 MPa. The pressure in the autoclave was reduced to −0.02 MPa over 8 hours, and thereafter returned to atmospheric pressure. The reaction product was washed with water.

99% of $CF_3CH_2OCF_2CHF_2$ fed for the polymerization was recovered as a mixture with TFE and ethylene in the recovery tank. The amount of fluororesin powder mixed into the recovered liquid along with the gas components was less than 0.001 kg.

The amount of fluororesin powder obtained was 39 kg. The fluororesin had a melting point of 245° C., and a MFR of 11.0. The compression ratio of the compressor was 7.5.

$CF_3CH_2OCF_2CHF_2$, TFE, and ethylene recovered in the recovery tank were transferred to a rectifier (multistage distillation column) made of SUS, and they were rectified (subjected to multistage distillation) to separate $CF_3CH_2OCF_2CHF_2$ from ethylene and TFE which had a boiling point lower than that of $CF_3CH_2OCF_2CHF_2$. $CF_3CH_2OCF_2CHF_2$ separated from ethylene and TFE was subjected to distillation using a simple distillation apparatus.

Example 15

(Polymerization Reaction)

A 175-L autoclave was charged with 42 L of distilled water, and sufficiently purged with nitrogen. Subsequently, 33 kg of perfluorocyclobutane (C318) was fed. The temperature in the system was maintained at 35° C., and the stirring rate was maintained at 235 rpm.

Thereafter, 1.67 kg of perfluoro(propyl vinyl ether) (PPVE) and 292 g of methanol were fed, and TFE was fed to 0.84 MPa. Thereafter, 73 g of a 50% by weight solution of di-n-propyl peroxydicarbonate (NPP)/$C_4F_9OCH_3$ (HFE7100) was fed as a polymerization initiator to initiate reaction.

As the pressure in the system drops with the progress of the polymerization, TFE was continuously fed to maintain the pressure in the system at 0.84 MPa. The reaction was stopped after 35 kg of TFE was fed in total.

(Solvent Recovery Step)

The temperature in the autoclave was set at 80° C., and the temperature in a recovery tank was set at 10° C. Gas components were transferred to the recovery tank from the gas phase portion in the autoclave using a compressor at a rate of about 6.3 kg/hour by adjusting the opening degree of a valve in this step. Gas components not liquefied in the cooling step were discharged from the recovery tank through a duct of the recovery tank to a gas holder to regulate the inner pressure of the recovery tank to the range of 0.6 to 0.8 MPa. The pressure in the autoclave was reduced to −0.02 MPa over 8 hours.

Next, 500 g of C318 was fed to the autoclave, and the contents in the autoclave were mixed for 30 minutes. The pressure in the autoclave was reduced to −0.02 MPa at a rate of about 1.1 kg/hour over 30 minutes by adjusting the opening degree of a valve in this step.

The steps of feeding C318 through reducing the pressure to −0.02 MPa in the recovery operation were repeated seven times, and thereafter the pressure was returned to atmospheric pressure. The reaction product was washed with water.

99% of $C_4F_9OCH_3$ fed for the polymerization was recovered as a mixture with C318 and TFE in the recovery tank. The amount of fluororesin powder mixed into the recovered liquid along with the gas components was less than 0.001 kg.

The amount of fluororesin powder obtained was 36 kg. The resulting fluororesin had a melting point of 304° C., and a MFR of 2.0. The compression ratio of the compressor was 7.5.

$C_4F_9OCH_3$, C318, and TFE recovered in the recovery tank were transferred to a rectifier (multistage distillation column) made of SUS, and they were rectified (subjected to multistage distillation) to separate $C_4F_9OCH_3$ from C318 and TFE which had a boiling point lower than that of $C_4F_9OCH_3$. $C_4F_9OCH_3$ separated from C318 and TFE was further subjected to distillation using a simple distillation apparatus.

Table 1 shows the recovering conditions and the recovery yields of Comparative Examples 1 to 3 and Examples 1 to 15.

TABLE 1

| | Comparative Example 1 | Comparative Example 2 | Comparative Example 3 | Example 1 | Example 2 | Example 3 | Example 4 | Example 5 | Example 6 |
|---|---|---|---|---|---|---|---|---|---|
| Fluororesin | FEP | FEP | FEP | FEP | FEP | FEP | FEP | FEP | FEP |
| Solvent | PFH | CFC113 | PFH | HFE7100 | HFE7100 | HFE7100 | HFE7100 | HFE7100 | HFE7100 |
| Recovery yield [%] | 80 | 80 | 65 | 99 | 99 | 90 | 90 | 90 | 90 |
| Transfer rate | 0.0286 | 0.0286 | 0.0286 | 0.0286 | 0.0086 | 0.0286 | 0.0486 | 0.0886 | 0.1257 |
| (x/V) [(kg/hr)/L] | 0.0074 | 0.0074 | — | 0.0074 | 0.0086 | — | — | — | — |
| Vaporization promoting substance | HFP | HFP | Absence | HFP | HFP | Absence | Absence | Absence | Absence |
| Compression ratio | 7.5 | 7.5 | 7.5 | 7.5 | 7.5 | 7.5 | 7.5 | 7.5 | 7.5 |
| Cooling temperature [° C.] | 10 | 10 | 10 | 10 | 10 | 10 | 10 | 10 | 10 |
| Amount of fluororesin in recovered liquid [kg] | <0.001 | <0.001 | <0.001 | <0.001 | <0.001 | <0.001 | <0.001 | 0.01 | 0.03 |

TABLE 1-continued

|  | Example 7 | Example 8 | Example 9 | Example 10 | Example 11 | Example 12 | Example 13 | Example 14 | Example 15 |
|---|---|---|---|---|---|---|---|---|---|
| Fluororesin | FEP | FEP | ETFE | ETFE | ETFE | ETFE | ETFE | ETFE | PFA |
| Solvent | HFE7100 | HFE7100 | HFE7100 | HFE7100 | HFE7100 | HFE7100 | HFE7000 | HFE-S7 | HFE7100 |
| Recovery yield [%] | 90 | 99 | 99 | 90 | 90 | 99 | 99 | 99 | 99 |
| Transfer rate | 0.1429 | 0.0057 | 0.0360 | 0.0360 | 0.0360 | 0.0360 | 0.0360 | 0.0360 | 0.0360 |
| (x/V) [(kg/hr)/L] | — | 0.0011 | 0.0063 | — | 0.0063 | — | — | — | 0.0063 |
| Vaporization promoting substance | Absence | HFP | C318 | Absence | C318 | Absence | Absence | Absence | C318 |
| Compression ratio | 7.5 | 7.5 | 7.5 | 7.5 | No data | 7.5 | 7.5 | 7.5 | 7.5 |
| Cooling temperature [° C.] | 10 | 10 | 10 | 10 | −20 | 10 | 10 | 10 | 10 |
| Amount of fluororesin in recovered liquid [kg] | 5 | <0.001 | <0.001 | <0.001 | <0.001 | <0.001 | <0.001 | <0.001 | <0.001 |

REFERENCE SIGNS LIST

11: Reaction vessel
12: Recovery container
21: Heating means
22: Valve
23: Cooling means
24: Discharge means

The invention claimed is:

1. A method for recovering a fluorine-containing ether, comprising the steps of:
   producing a wet fluoropolymer by suspension polymerization, solution polymerization, or bulk polymerization in the presence of at least a fluorine-containing ether represented by the formula (1):

$$Rf—O—R \quad (1)$$

wherein Rf represents a C2-C6 fluoroalkyl group or a C2-C6 alkyl group, and R represents a C1-C4 fluoroalkyl group or a C1-C4 alkyl group, provided that the total number of carbon atoms in Rf and R is at most 8;
   vaporizing and discharging vaporizable substances including the fluorine-containing ether by heating the wet fluoropolymer in a container; and
   transferring the vaporizable substances in the vaporized state to a cooling means to cool the vaporizable substances, and
   wherein a value of x/V is at most 0.140,
   wherein V represents the inner volume (L) of the container, and x represents the discharge rate (kg/hour) of the vaporizable substances from the container.

2. The method for recovering a fluorine-containing ether according to claim 1,
   wherein the fluoropolymer has a polymerization unit derived from at least one fluoromonomer selected from the group consisting of tetrafluoroethylene, hexafluoropropylene, vinylidene fluoride, chlorotrifluoroethylene, (perfluoromethyl)vinyl ether, (perfluoroethyl)vinyl ether, (perfluoropropyl)vinyl ether, trifluoroethylene, vinyl fluoride, perfluoro(alkyl vinyl ethers) represented by the formula (2-1):

$$CF_2=CFO(CF_2CF(Y)O)_m(CF_2)_nF \quad (2-1)$$

wherein Y represents a fluorine atom or a trifluoromethyl group, m is an integer of 0 to 2, and n is an integer of 1 to 4, monomers represented by the formula (2-2):

$$CH_2=CF(CF_2)_nZ \quad (2-2)$$

wherein Z represents a fluorine atom or a hydrogen atom, and n is an integer of 1 to 8, and monomers represented by the formula (2-3):

$$CH_2=CH(CF_2)_nZ \quad (2-3)$$

wherein Z represents a fluorine atom or a hydrogen atom, and n is an integer of 1 to 8.

3. The method for recovering a fluorine-containing ether according to claim 1, further comprising a step of transferring the vaporizable substances liquefied by cooling in the cooling step to a distillation means to distill the vaporizable substances.

4. The method for recovering a fluorine-containing ether according to claim 1,
   wherein a fluorine-containing compound having a boiling point lower than the boiling point of the fluorine-containing ether is added to the wet fluoropolymer.

5. The method for recovering a fluorine-containing ether according to claim 1, further comprising a step of transferring the vaporizable substances vaporized in the vaporizing step to a compression means to compress the vaporizable substances.

6. The method for recovering a fluorine-containing ether according to claim 5,
   wherein the compression means is a compressor.

7. The method for recovering a fluorine-containing ether according to claim 1,
   wherein the cooling means is a condenser.

* * * * *

UNITED STATES PATENT AND TRADEMARK OFFICE
CERTIFICATE OF CORRECTION

PATENT NO. : 9,475,744 B2  Page 1 of 1
APPLICATION NO. : 14/654238
DATED : October 25, 2016
INVENTOR(S) : Zenke et al.

It is certified that error appears in the above-identified patent and that said Letters Patent is hereby corrected as shown below:

On the Title Page

Item [73], change "DAIKAN" to --DAIKIN--.

Signed and Sealed this
Sixth Day of June, 2017

Michelle K. Lee
*Director of the United States Patent and Trademark Office*